US012797636B2

(12) United States Patent
Dupont et al.

(10) Patent No.: US 12,797,636 B2
(45) Date of Patent: Nov. 17, 2026

(54) SYSTEM FOR A PHOTODYNAMIC THERAPY TREATMENT

(71) Applicant: HEMERION THERAPEUTICS, Villeneuve d'Ascq (FR)

(72) Inventors: Clément Dupont, Lille (FR); Simon Lanet, La Fresnaye sur Chédouet (FR); Maximilien Vermandel, Neuville en Ferrain (FR)

(73) Assignee: HEMERION THERAPEUTICS, Villeneuve d'Ascq (FR)

( * ) Notice: Subject to any disclaimer, the term of this patent is extended or adjusted under 35 U.S.C. 154(b) by 289 days.

(21) Appl. No.: 18/567,918

(22) PCT Filed: Jun. 9, 2022

(86) PCT No.: PCT/EP2022/065621
§ 371 (c)(1),
(2) Date: Dec. 7, 2023

(87) PCT Pub. No.: WO2022/258727
PCT Pub. Date: Dec. 15, 2022

(65) Prior Publication Data

US 2024/0366958 A1 Nov. 7, 2024

(30) Foreign Application Priority Data

Jun. 9, 2021 (EP) .................................... 21305784

(51) Int. Cl.
*A61N 5/06* (2006.01)

(52) U.S. Cl.
CPC ........... *A61N 5/062* (2013.01); *A61N 5/0622* (2013.01); *A61N 2005/0644* (2013.01)

(58) Field of Classification Search
CPC .................. A61N 5/062; A61N 5/0622; A61N 2005/0644; A61N 5/0603;
(Continued)

(56) References Cited

U.S. PATENT DOCUMENTS 4,612,938 A 9/1986 Dietrich et al.
4,998,930 A * 3/1991 Lundahl ............... A61N 5/0603 606/15
(Continued)

FOREIGN PATENT DOCUMENTS

CN 106345040 A 1/2017
JP H07503163 A 4/1995
(Continued)

OTHER PUBLICATIONS

Hamblin, Michael R., Ana P. Castano, and Pawel Mroz. "Combination immunotherapy and photodynamic therapy for cancer." Proceedings of Light-Activated Tissue Regeneration and Therapy Conference, Springer Science+ Business Media, Berlin. 2008. (Year: 2008).*
(Continued)

*Primary Examiner* — Jonathan T Kuo
(74) *Attorney, Agent, or Firm* — Maier & Maier, PLLC

(57) ABSTRACT

A photodynamic therapy treatment of a cavity for providing a predetermined dose of light energy, the cavity being delimited by cells with photosensitizers, having: an external hollow rod, an internal hollow rod to be inserted inside the external rod, an inflatable balloon secured on the external rod, the inside of the balloon being in fluidic communication with the inside of it, a handle made of one single piece. The handle receives an illuminating device for illuminating the balloon to activate the photosensitizers. The handle and the rods are sealingly secured to each other in one single screwing movement. An illumination time is determined by means of a transfer function relating each volume of the balloon to at least one corresponding distribution of light power at its outer surface and a corresponding illumination time for providing the energy dose.

17 Claims, 6 Drawing Sheets

(58) Field of Classification Search
CPC .... A61N 2005/0626; A61N 2005/0632; A61B 18/20–18/28
See application file for complete search history.

(56) References Cited

U.S. PATENT DOCUMENTS

| | | | | |
|---|---|---|---|---|
| 11,135,443 | B2 * | 10/2021 | Vermandel | A61N 5/0603 |
| 2003/0236495 | A1 | 12/2003 | Kennedy, II | |
| 2008/0306441 | A1 * | 12/2008 | Brown | A61M 25/10<br>604/99.01 |
| 2011/0098687 | A1 | 4/2011 | Chan et al. | |
| 2019/0328523 | A1 | 10/2019 | Poppe et al. | |
| 2020/0289840 | A1 * | 9/2020 | Vermandel | A61N 5/062 |

FOREIGN PATENT DOCUMENTS

| | | | | |
|---|---|---|---|---|
| JP | 2019509878 | A | 4/2019 | |
| JP | 2021521981 | A | 8/2021 | |
| WO | 9314805 | A1 | 8/1993 | |
| WO | 03097152 | A1 | 11/2003 | |
| WO | 2009005779 | A1 | 1/2009 | |
| WO | WO-2017162869 | A1 * | 9/2017 | A61N 5/067 |
| WO | 2019210165 | A1 | 10/2019 | |

OTHER PUBLICATIONS

International Search Report issued on Sep. 16, 2022, in corresponding International Patent Application No. PCT/EP2022/065621, 5 pages.

* cited by examiner

SYSTEM FOR A PHOTODYNAMIC THERAPY TREATMENT

FIELD

The invention relates to a system for treatment by photodynamic therapy of a cavity of a patient's body and to a method for preparation of such system.

Although not limited thereto, the invention finds particular application in neurosurgery and especially in surgical resection of a glioblastoma.

BACKGROUND

A glioblastoma is the most frequent malignant primitive cerebral tumor for an adult, with an incidence in France of 4/100,000. It is however considered as a rare disease. With a conventional treatment involving in particular surgery and radio-chemotherapy, the survival median is 14.5 months. The invasive nature of the glioblastoma explains in part its unavoidable recurrence. In spite of a radiologically complete resection, tumor cells infiltrated in adjacent healthy tissues are insufficiently treated by a supplemental radio-chemotherapy and, recurrence then occurs in over 80% of the cases adjacent to the resection cavity. It has been shown in numerous studies that the quality of the surgical resection is a major prognostic factor.

Hence, optimization of a local control of the quality of the surgical resection is a significant challenge to improve survival without progression of the tumor and thereby to improve the global survival.

With respect to such optimization, association with photodynamic therapy (PDT) delivered to the edges of the resection cavity has been considered. Photodynamic therapy relies on the interaction of three components: a photosensitizer compound, oxygen within the tissues and light having properties suitable for activating the photosensitizer compound. The photosensitizer compound injected within the body of the patient is absorbed by all cells but remains a longer time within tumour cells. Upon activation of the photosensitizer compound by the light, photo-chemical reactions occur resulting in the destruction of the tumour cells.

An example of a treatment by photodynamic therapy of glioblastoma is disclosed by Lyons et al. in "*The effects of PDT in primary malignant brain tumours could be improved by intraoperative radiotherapy*", Photodiagnosis and Photodynamic Therapy, 2012, 9 (1): 40-45. The known system for treatment by photodynamic therapy is of the type comprising an illuminating device intended for illuminating the cavity to be treated. The illuminating device comprises an illuminating member extending along a central axis between opposed proximal and distal ends. The illuminating member comprises:

- a core carrying a light emitting surface for emitting a light adapted to activate the photosensitizer compound, the light emitting surface being arranged at the distal end of the illuminating member, and
- a hollow sheath having a balloon arranged at the distal end of the illuminating member, the sheath being adapted to receive the core with the light emitting surface arranged within the balloon, the balloon comprising a wall which has an inner surface delimiting an internal space, and an outer surface, the wall being flexible and adapted to allow diffusion of the light emitted by the light emitting surface, the balloon presenting an inflated state in which the wall has a symmetry of revolution about the central axis and the internal space is filled with a light diffusing solution so as to diffuse the light emitted by the light emitting surface, and a deflated state in which the internal space is empty.

However, the known system has not allowed to significantly improve survival. In particular, such systems globally fail to deliver a standardized and controlled treatment in terms of fluence (J/cm$^2$) or efficient pattern light exposure.

The invention aims to solve the above-mentioned problems in providing a system which is easier, thus safer, to set up and assemble than the systems of the state of the art.

The current invention further aims at providing a handy, precise, easy to assemble and easy to handle system to do so. Such a system reduces the necessary time to operate and thus considerably lowers the risks associated with anesthesia. An easy-to-handle system further reduces manipulation risks and sterilization breaks.

SUMMARY

This invention thus relates to a system for a photodynamic therapy treatment of a patient's body cavity configured to provide a predetermined dose of light energy to said cavity, the cavity being delimited by tissues comprising cells having a photosensitizer compound or a precursor thereof absorbed therein, the system comprising:

- an external hollow rod extending along a central axis and displaying a distal extremity,
- an internal hollow rod configured to be inserted inside the external hollow rod, the internal hollow rod extending along the central axis and displaying a distal extremity, the distal extremity being at least partially transparent,
- an inflatable balloon secured on the distal extremity of the external hollow rod, the inside of the inflatable balloon being in fluidic communication with the inside of the external hollow rod, the inflatable balloon displaying a symmetry of revolution around the central axis, and being designed to either be vacuumized, or be filled, in a controlled way, with a fluid up to a given volume,
- a handle comprising two openings, a first opening connected to the inside of the internal hollow rod and a second opening connected to the inside of the external hollow rod.

In this system, the inside of the internal hollow rod is isolated from the inside of the external hollow rod, the handle is made of one single piece, the first opening of the handle is designed to receive, in a sealed way, an illuminating device intended for illuminating the inflatable balloon, the illuminating device being designed to emit a light adapted to activate the photosensitizer compound, the second opening of the handle is designed to be connected to a pumping device, the handle, the external rod and the internal rod are designed to be sealingly secured to each other in one single screwing movement, a given illumination time is determined by means of a transfer function relating each given volume of the inflatable balloon to at least one corresponding distribution of light power at the outer surface of the inflatable balloon and a corresponding illumination time for providing the predetermined dose of light energy.

This way, this solution enables to treat any kind of cavities. As the volume of the inflatable balloon can be adapted to the size of any cavity, and as the distribution of light power corresponding to the volume of the inflatable balloon is known, it is possible to deliver the appropriate dose of light energy in a complete and homogeneous manner.

The system according to the invention may comprises one or several of the following features, taken separately from each other or combined with each other:

- the inflatable balloon can be adapted to allow diffusion of the light emitted by the illuminating device,
- the inflatable balloon can have a variable capacity, the balloon being elastic and reversibly extendible, the inflatable balloon presenting a plurality of inflated states depending on the amount of fluid comprised inside the inflatable balloon,
- the transfer function can relate the volume of each inflated state of the inflatable balloon with at least one of the corresponding distributions of light power at the outer surface of the inflatable balloon and the corresponding illumination time for providing a determined dose of light energy,
- the inflatable balloon can display an elongated shape,
- the distal extremity of the internal hollow rod can be designed to be in permanent contact with the inflatable balloon,
- the internal hollow rod can comprise a slidable element, slidable along the central axis, in order to enable a permanent contact between the inflatable balloon and the distal extremity of the internal hollow rod,
- the handle, the external rod and the internal rod are designed to be sealingly secured to each other in one single screwing movement,
- the internal hollow rod can comprise a positioning device adapted to lock a distal extremity of the illuminating device inserted inside the internal hollow rod at a desired distance from the tip of the distal extremity of the internal hollow rod,
- the internal hollow rod can be flexible,
- the internal hollow rod can display centering means configured to center said internal hollow rod with regards to the central axis.

The invention further related to a kit for a photodynamic therapy treatment of a patient's body cavity configured to provide a predetermined dose of light energy to said cavity, wherein the kit comprises a system according to any one of the technical features described above, an illumination device configured to be inserted in said system and a control unit configured to control the illumination device.

The invention further relates to a method for preparation of a system for photodynamic therapy treatment according to one or several of the here-above listed features, the method comprising repeatedly performing steps of:

- inserting the internal hollow rod inside the external hollow rod,
- connecting the handle on the external hollow rod,
- inserting the illuminating device inside the internal hollow rod, through the first opening of the handle,
- positioning and/or locking the illuminating device at a predetermined distance from the tip of the distal extremity of the internal hollow rod,
- sealingly securing the handle, the internal hollow rod and the hollow external rod,
- connecting the second opening of the handle to the pumping device,
- vacuuming, by means of the pumping device, the inflatable balloon in order to completely emptying it and enable a precise determination of the size of the emptied balloon in order to set a referential,
- filling, by means of the pumping device, the inflatable balloon with a given volume fluid, and
- determining the illumination time by means of the transfer function.

The invention also relates to a method for treating cancer by photodynamic therapy in a patient in need thereof, the method comprising the steps of:

- administering a photosensitizer compound or a precursor thereof to the patient,
- providing a system according to any one of the here-above listed features, or preparing a system according to the method also described here-above,
- positioning the inflatable balloon of the system in a body cavity of the patient,
- activating the illuminating device,
- disactivating the illuminating device,
- optionally, repeating once or several times the two previous steps.

According to this method, the inflatable balloon can be deflated between two activations of the illuminating device, and the method can further comprise the step of treating the patient with an immunotherapy treatment before, concomitantly with and/or after photodynamic therapy.

BRIEF DESCRIPTION OF THE DRAWINGS

The invention will be better understood, and other aims, details, characteristics and advantages thereof will emerge more clearly on reading the detailed description which follows, of one or several embodiments of the invention given by way of illustration. Those are purely illustrative and non-limiting examples, with reference to the accompanying schematic drawings.

On these drawings.

DETAILED DESCRIPTION

Figure 1:
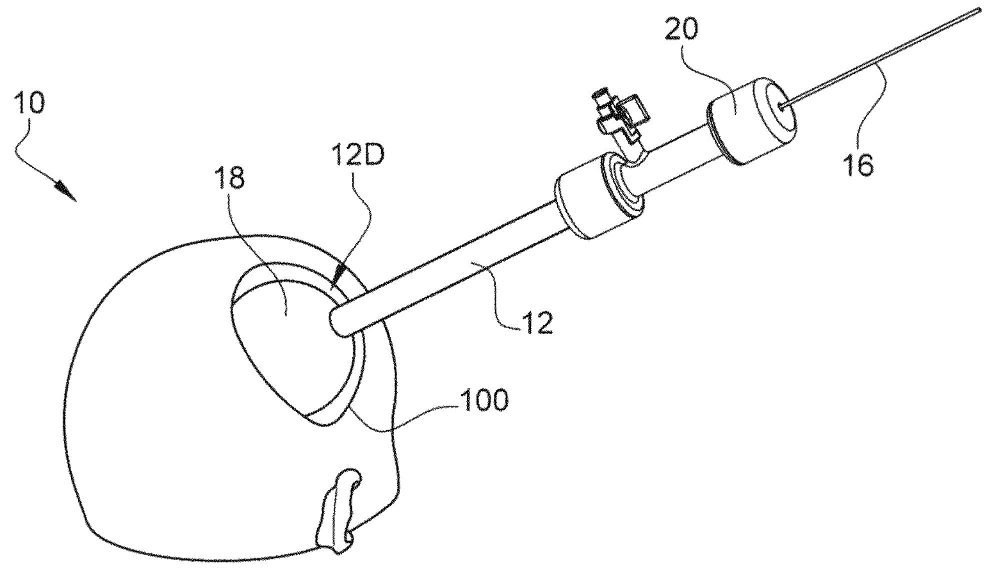
FIG. 1 is a schematical view of an embodiment of the system according to the present invention inserted inside a patient's body cavity.

As can be seen on FIG. 1, a system 10 for a photodynamic therapy treatment of a patient's body cavity 100 according to the present invention comprises:

- an external hollow rod 12 (see FIG. 3*a*),
- an internal hollow rod 14 (see FIG. 3*b*),
- an illuminating device 16,
- an inflatable balloon 18,
- a handle 20.

The system 10 according to the present invention is aimed to be connected to a pumping device 22 a fluid reservoir 23.

In one embodiment, the patient's body cavity 100 is a natural body cavity, i.e., a space or compartment that accommodates organs and other structures. Natural body cavities also include so-called "potential spaces" or "serous membrane cavities", i.e., spaces between two adjacent structures that are typically more or less pressed together (in other words, directly apposed) and that open up upon physiologic or pathophysiologic events. Examples of natural body cavities include, without limitation, the dorsal body cavity (including the cranial cavity and the spinal cavity) and the ventral body cavity (including the thoracic cavity, the abdominal cavity and the pelvic cavity). Examples of potential spaces include, without limitation, the two pleural cavities (right and left), the superior mediastinum, the pericardial cavity, and the peritoneal cavity. Each body cavity and potential space may be subdivided into subcavities or subspaces that are well known to the skilled artisan.

In one embodiment, the patient's body cavity 100 is a surgically-created resection cavity, i.e., a space that is left after the surgical removal of a body part, such as, e.g., a tissue, an organ or a part thereof, or a tumor; in particular a solid tumor.

By "solid tumors" are meant tumors and/or metastasis (wherever located) other than lymphatic cancer, including, but not limited to, e.g., brain and other central nervous system tumors (such as tumors of the meninges, brain, spinal cord, cranial nerves or other parts of central nervous system, e.g., glioblastomas or medulla blastomas); head and/or neck cancer; breast tumors; circulatory system tumors (such as tumors of the heart, mediastinum, pleura, or of other intrathoracic organs, as well as vascular tumors); excretory system tumors (such as tumors of the kidney, renal pelvis, ureter, bladder, or of other urinary organs); gastrointestinal tract tumors (such as tumors of the esophagus, stomach, small intestine, colon, colorectal, rectosigmoid junction, rectum, anus or anal canal), liver tumors (such as hepatocellular carcinoma), intrahepatic bile ducts tumors, gall bladder tumors, biliary tract tumors, pancreatic tumors, and tumors of other digestive organs; head and neck tumors; oral cavity tumors (such as tumors of the lip, tongue, gum, floor of mouth, palate, or of other parts of mouth, as well as parotid gland tumors, salivary gland tumors, as well as tumors of the tonsil, oropharynx, nasopharynx, pyriform sinus, hypopharynx, or of other sites in the lip, oral cavity or pharynx); reproductive system tumors (such as tumors of the vulva, vagina, cervix uteri, corpus uteri, uterus, ovary, or of other sites associated with female genital organs, as well as tumors of the penis, prostate, testis, or of other sites associated with male genital organs); respiratory tract tumors (such as tumors of the nasal cavity, middle ear, accessory sinuses, larynx, trachea, bronchus, pleura or lung, e.g., small cell lung cancer, non-small cell lung cancer or malignant pleural mesothelioma); skeletal system tumors (such as tumors of the bones, articular cartilage of limbs, or bone articular cartilage); skin tumors (such as malignant melanoma of the skin, non-melanoma skin cancer, basal cell carcinoma of skin, squamous cell carcinoma of skin, mesothelioma, Kaposi's sarcoma).

Among the tumors listed above, some of them can start in a natural body cavity, and those are referred in the art to as "serosal cancers". Examples of such serosal cancers include, without limitation, nasal cancer, oral cancer, mesothelioma, malignant pleural mesothelioma, pleural metastasis, bladder cancer, uterine cancer, pancreatic cancer, esophageal cancer, stomach cancer and peritoneal carcinomatosis.

In one embodiment, the photodynamic therapy treatment may be intraoperative, that is to say, performed during the same medical procedure as the resection of the body part or tumor; or post-operative, that is to say, performed after the resection of the body part or tumor, during a separate medical procedure.

In a particular embodiment, the solid tumor is a glioblastoma, and the patient's body cavity 100 results from the resection of the glioblastoma.

In a particular embodiment, the solid tumor is malignant pleural mesothelioma, and the patient's body cavity 100 is the pleural cavity.

In a particular embodiment, the solid tumor is hepatocellular carcinoma and the patient's body cavity 100 results from the resection of the hepatocellular carcinoma, or alternatively the patient's body cavity 100 is the abdominal cavity, e.g., the supramesocolic space.

In a particular embodiment, the solid tumor is a pancreatic tumor, and the patient's body cavity 100 results from the resection of the pancreatic tumor.

Figure 3A:
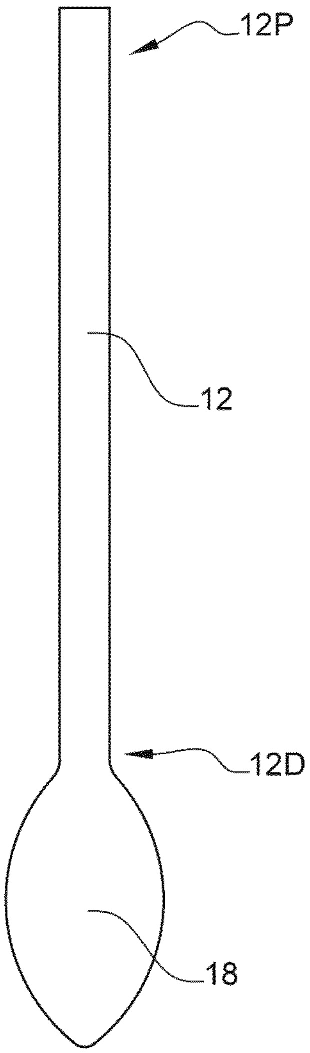
FIG. 3*a* is a schematical view of an external hollow rod according to the present invention.
Figure 5:
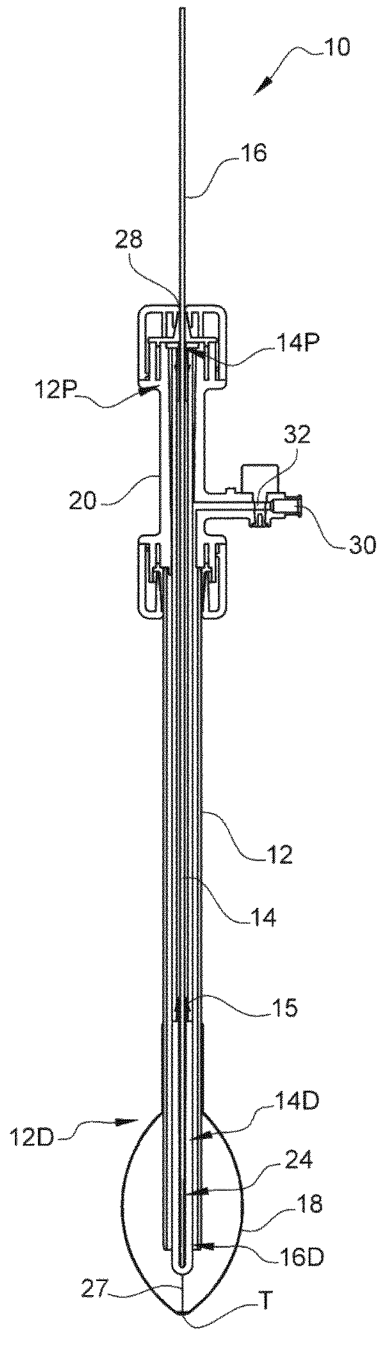
FIG. 5 is a longitudinal section view of an embodiment of the system according to the present invention.
Figure 6:
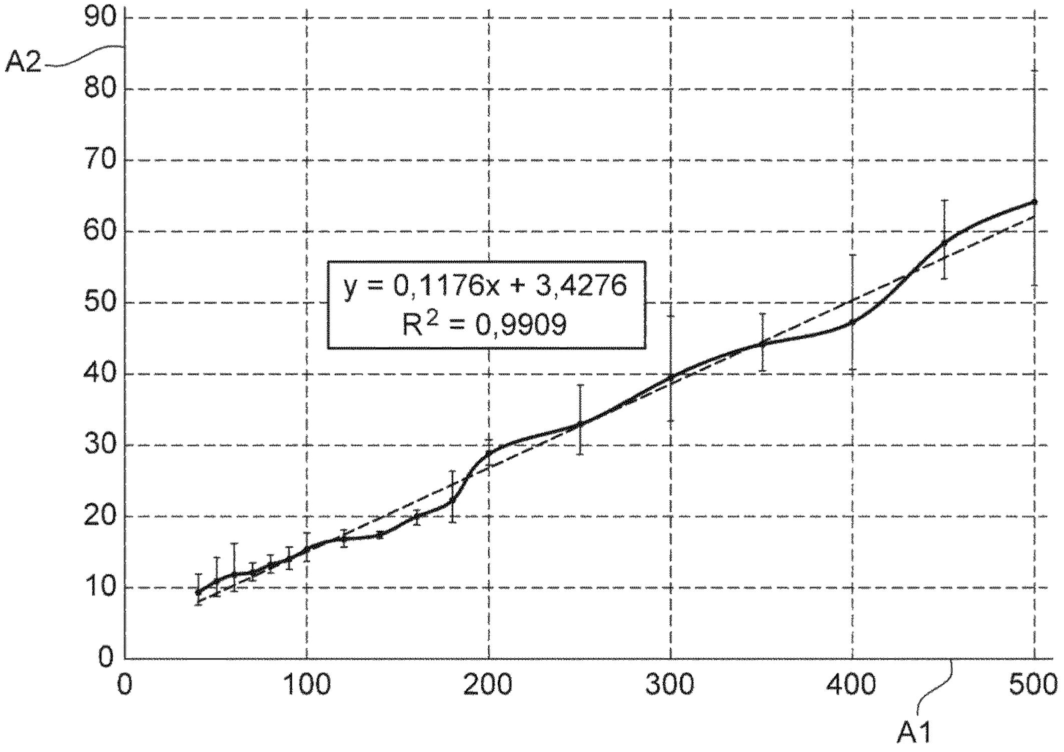
FIG. 6 is a graphic illustration of the transfer function of the system according to the present invention.

As can be seen on FIGS. 3*a* and 5, the external hollow rod 12 extends along a central axis X and displays a proximal extremity 12P and a distal extremity 12D.

The external hollow rod 12 is preferably made of a biocompatible material allowing diffusion of the light emitted by the light emitting device 16, especially a transparent or translucent material. The external hollow rod 12 is preferably rigid. The external hollow rod 12 might be a trocar alike device. It is aimed to be used by the operator, to insert and guide the inflatable balloon 18 through the patient's body towards and into the cavity 100. The external hollow rod 12 is configured to be connected to the fluid reservoir 23 and be put in fluidic communication with said fluid reservoir 23 by means of the pumping device 22. The pumping device 22 may be a passive or an active pumping device 22. It might be manually or electronically activable. It might, for example, be a syringe type (of for example 50 mL) of pumping device.

Figure 3B:
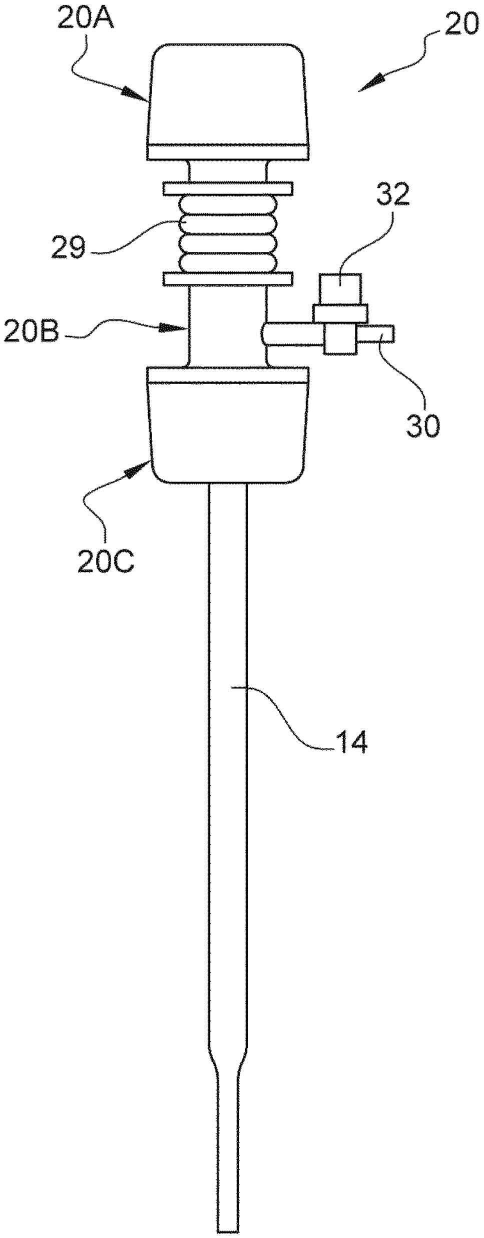
FIG. 3*b* is a schematical view of an internal hollow rod according to the present invention.
Figure 4:
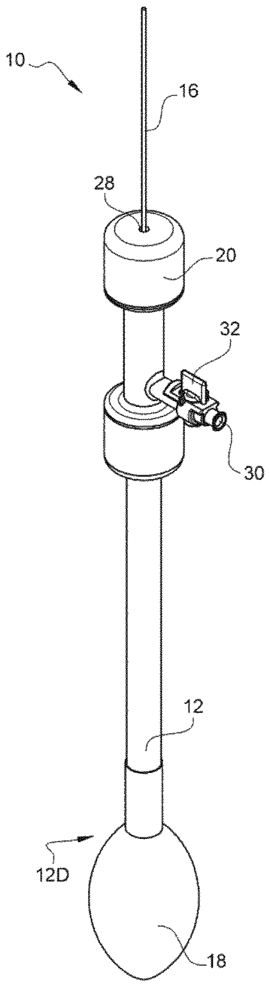
FIG. 4 is a perspective detailed view of an embodiment of the system according to the present invention.

As can be seen on FIGS. 3*b*, 4 and 5, the internal hollow rod 14 also extends along the central axis X and also displays a proximal extremity 14P and a distal extremity 14D. The internal hollow rod 14 might be made of polypropylene. The distal extremity 14D of the internal rod 14 is at least partially transparent, and comprises thus a transparent part 24. Said transparent part can for example be made of styrene methyl methacrylate. The length of the at least partially transparent part 24 of the distal extremity 14D of the internal rod 14 is comprised between 50 and 100 mm. The internal rod 14 is configured to be inserted inside the external hollow rod 12. The external and internal rods 12, 14 both present a length comprised between 50 and 150 cm. The external hollow rod presents a width comprised between 7 and 12 cm while the internal hollow rod 14 presents a width comprised between 2 and 4 cm. The external follow rod 12 presents a length.

The internal hollow rod 14 might be made of polypropylene and is thus flexible. In order to ensure the centering of the internal hollow rod 14 along the central axis X inside the external hollow rod 12, the internal hollow rod 14 displays centering means 25 configured to center said internal hollow rod 14 with regards to the central axis X.

The inside of the internal hollow rod 14 is configured to receive at least part of the illuminating device 16 and is therefore isolated from the inside of the external hollow rod 12 in order to seal the illuminating device 16 away from any possible fluid circulating inside the external hollow rod 12. The system 10 according to the present invention comprises a positioning device 15. This positioning device 15 aims at correctly positioning the illuminating device 16 inside the internal hollow rod 14 in order to maximize the efficiency of the system 10. In some embodiments, the positioning device is located inside the handle 20. In another embodiment, the positioning device is located inside the internal hollow rod 14. In this embodiment, the positioning device 15 is adapted to lock a distal extremity 16D of the illuminating device 16 inserted inside the internal hollow rod 14 at a desired distance from the tip T of the distal extremity 14D of the internal hollow rod 14. In this embodiment, this positioning device 15 can for example be an abutment piece situated at a specific distance from the tip of the internal hollow rod 14 inside said internal hollow rod 14, or a graduated scale enabling to adjust the positioning of the distal extremity 16D of the illuminating device 16 and then locking it by means, for example, of pinching element situated in the handle 20. The positioning device 15 aims at locking the illuminating device 16 in order to optimize its position regarding the partially transparent part 24 of the distal extremity 14D of the internal rod 14 [to be confirmed].

Figure 2:
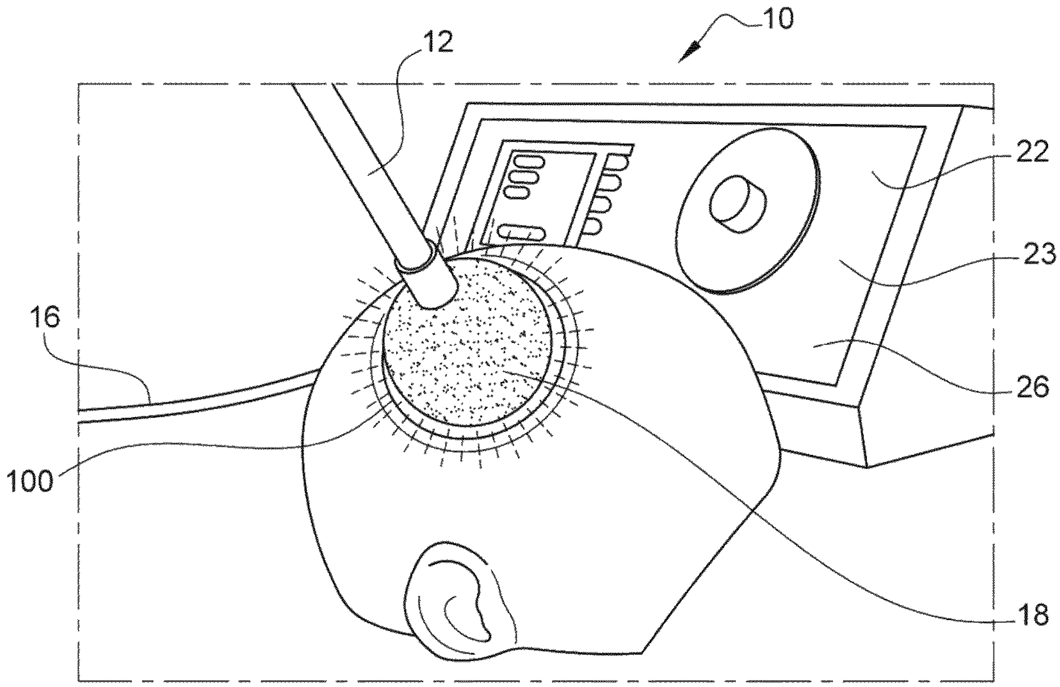
FIG. 2 is a schematical view of an embodiment of the system according to the present invention in use inside a patient's body cavity.

The illuminating device 16 is designed to emit a light. In one embodiment, the light is adapted to activate a photosensitizer compound absorbed by the tissues delimiting the patient's body cavity 100, or otherwise metabolized in these tissues from a photosensitizer compound precursor, as can be seen on FIG. 2. As already stated in the above, the photodynamic therapy (PDT) treatment relies upon activation of the photosensitizer compound, said photosensitizer compound (or precursor thereof) having been previously administered to the patient and absorbed by the cells of the tissues delimiting the patient's body cavity 100. This activation necessitates a specific light, said light displaying physical features enabling the destruction of the tumorous cells in which the photosensitizer compound is preferentially accumulated. The system 10 according to the present invention is thus configured to provide a predetermined dose of light energy to said cavity 100, the cavity 100 being delimited by tissues comprising cells having a photosensitizer compound absorbed therein.

Examples of photosensitizer compounds and precursors thereof are well known in the art. These include, without limitation, porphyrins, chlorins and dyes. Specific examples include, without limitation, 5-aminolevulinic acid (ALA), verteporfin, etiopurpurin, tetra(m-hydroxyphenyl) chlorin (mTHPC), motexafin lutetium, 9-acetoxy-2,7,12,17-tetrakis-(β-methoxyethyl)-porphycene (ATMPn), zinc phthalocyanine, naphtalocyanines, porfimer sodium, meso-tetrahydroxyphenylchlorin, methyl aminolevulinate, hexyl aminolevulinate, mono-L-aspartyl chlorin e6 (NPe6), 2-(1-hexyloxyethyl)-2-devinyl pyropheophorbide-a (HPPH), sulfonated aluminium phthalocyanines, azadipyrromethenes, silicon phthalocyanine (Pc 4), and salts, prodrugs, and derivatives thereof.

In one embodiment, the precursor of the photosensitizer compound is 5-aminolevulinic acid, commercially available under the tradenames Gliolan® (Medac GmbH), Gleolan® (NX Development Corp), Levulan® (DUSA Pharmaceuticals, Inc.), or Ameluz® (Biofrontera Bioscience GmbH).

In one embodiment where the photodynamic therapy treatment is intraoperative, that is to say, performed during the same medical procedure as the resection of the body part or tumor, the photosensitizer compound can be administered to the patient prior to the medical procedure, first to enable the surgeon to perform a visual prognostic of the tumor inside the cavity 100, and then, upon metabolization, to be used as photosensitizer for the photodynamic therapy.

More precisely, the illuminating device 16 is intended for illuminating the inflatable balloon 18. The illuminating device 16 may be an optical fiber connected to a laser light source. Said light source might be a frontal or a cylindrical or a spherical light source. It might comprise a single or multiple rings light diffusion tips.

The illuminating device 16 might be activated for a long period of time (for example up to two hours continuously), or might be successively activated and inactivated over shorter period of times, thus providing variable illumination times.

This enables two different types of treatments:

- a continuous treatment type during which the illuminating device 16 can be activated continuously for several minutes or hours ("always-on" illumination),
- a fractionated treatment type which comprises a succession of "ON times" and "OFF times" during which the illuminating device 16 is respectively activated and inactivated (on/off illuminations), each "time ON" and "time OFF" independently from each other lasting several seconds or minutes.

More particularly, each given illumination time is determined by means of a transfer function relating any given volume V of the balloon 18 to at least one corresponding distribution of light power at the outer surface of the inflatable balloon 18 and a corresponding illumination time for providing the necessary, predetermined dose of light energy.

The illumination time may be manually controlled by an operator on the basis of the transfer function associating each value of a range of volumes V of the inflatable balloon 18 to at least one of:

- a set of values of light power at the outer surface of the inflatable balloon 18, and
- an illumination time for providing the determined dose of light energy.

In a variant, the illumination time may be automatically controlled by a control unit 26. For example, for a volume of 53 mL, the control unit 26 calculates the corresponding illumination time for a predetermined dose of light energy, for example 25 J/cm$^2$. The usual energy dose necessary for activating the photosensitizer compound is well known in the art, and may range from about 1 J/cm$^2$ to about 40 J/cm$^2$.

An example of the transfer function is to be seen on FIG. 5, on which the illumination time in minutes (Axis A2) is expressed in function of an injected light diffusing solution volume V in mL (Axis A1). The injected fluid volume V corresponds to the volume V of the inflatable balloon 18. As can be seen on FIG. 5, each volume of light diffusing solution is related to a corresponding time of illumination for providing the determined dose of light energy.

The inflatable balloon 18 is secured on the distal extremity 12D of the external hollow rod 12. The inside of the inflatable balloon 18 is in fluidic communication with said inside of the external hollow rod 12, thus allowing any fluid flowing through the inside of the external hollow rod 12 to enter the inflatable balloon 18.

The inflatable balloon 18 is adapted to allow diffusion of the light emitted by the illumination device 16 and more particularly by the at least partially transparent part 24 of the distal extremity 14D of the internal rod 14.

The inflatable balloon 18 displays elastic properties, has a variable capacity and thus a variable volume V. It can thus be filled, with any kind of fluid from the fluid reservoir 23, in order to be expanded up to any given volume equal or below its maximal capacity of 1.5 L. In the context of the present invention, the inflatable balloon 18 is preferably filled with a light diffusing solution. In particular, a light diffusing solution of a concentration of 0.1% may be prepared by injecting 5 mL of intralipide® liquid, such as an intralipid liquid with a concentration of 20% exploited by the company Fresenius Kabi France, in 1L of physiological serum to form a mixture that is agitated until a homogeneous solution is obtained.

As the inflatable balloon 18 is reversibly extendible, it presents a plurality of inflated states depending on the amount of fluid injected inside the inflatable balloon 18. The inflatable balloon 18 can thus either be vacuumized or be filled, in a controlled way, with fluid in order to control its volume V and thus to adapt said volume V to the patient's body cavity 100. Therefore, the transfer function relates the volume V of each inflated state with at least one of a corresponding distribution of light power at the outer surface of the inflatable balloon 18 and a corresponding illumination for providing a determined dose of light energy. Each given volume V or inflated state is determined by the size of the patient's body cavity 100. More precisely, during operation, the inflatable balloon 18 is conformed to the patient's body cavity 100 by filling its entire internal space. The inflatable balloon 18 is thus filled with fluid and therefore inflated (expanded) until the wall of the inflatable balloon 18 comes in contact with tissues delimiting the cavity 100.

The inflatable balloon 18 is either inflated manually or by means of the pumping device 22. given volume V of the inflatable balloon 18 is either noted by the operator or stored by the control unit 26. The pumping device 22 might also be controlled by the control unit 26.

In order to ensure a regular and homogeneous light diffusion inside the cavity, the inflatable balloon 18 displays a symmetry of revolution around the central axis X. The inflatable balloon 18 is preferably made of transparent or translucid silicone.

In order to be more easily moved through the patient's body towards and inside the cavity 100, the inflatable balloon 18 preferably displays an elongated shape.

In order to improve the stability of the inflatable balloon 18, and maintain it centered and fully extended when inflated, the distal extremity 14D of the internal hollow rod 14 is designed to be in permanent contact with the balloon 18, for example by means of a slidable element 27 (see FIG. 5), connected to either the proximal or the distal extremity 14P, 14D of the internal hollow rod 14. This slidable element 27 is slidable along the central axis X and enables a permanent contact between the inflatable balloon 18, preferably the tip of the inflatable balloon 18, and the distal extremity 14D of the internal hollow rod 14.

The handle 20 enables the system 10 to be safely manipulated by the operator during the operation. The handle 20 further enables the system 10 to be safely secured to a classical carrying device usually present in any operation room. Those carrying devices are usually known as "instrument holding arms". With regards to said manipulation, the handle 20 displays an ergonomic shape to render it easy to grab for the operator. In some embodiments the handle 20 further comprises a circular grabbing zone 29 (see FIG. 3*b*) specially designed for an articulated arm to grab it safely, thus enabling the safe maintaining of the system 10 in a given position during activation of the illuminating device 26. In some embodiment (see FIG. 4), the handle 20 is made of one single piece and is to be connected to the proximal extremity 12P of the external hollow rod 12 and to the proximal extremity 14P of the internal hollow rod 14. Made of one single piece, the handle 20 can thus be used and secured to the external and internal hollow rods 12, 14 without the necessity of adding sealing elements or joints to achieve fluid tightness, thus improving the practicability and the efficiency of the handle 20 and thus the system 10. As the handle 20 is made from one single piece, it further allows an easy manual "once gesture" securing of the handle 20 to the external and internal rods 12, 14. The fact that the handle 20 is made of one single piece directly enables, the handle, 20, the external rod 12 and the internal rod 14 to be sealingly secured to each other in one single screwing movement; In some embodiments, the handle 20 may comprise several parts 20A, 20B, 20C which might be movable with regards to each other. However, in those embodiments, the handle 20 is still considered as being one single piece as those different parts 20A, 20B, 20C cannot be detached from each other, the handle 20 still having to be manipulated as one single independent technical element, with no necessity of adding sealing elements or joints to achieve fluid tightness.

Alternatively, in the embodiment depicted on FIG. 3*b*, the handle 20 comprises three, relatively to each other, mobile parts 20A, 20B and 20C. The three parts 20A, 20B and 20C are all aligned along the central axis X. The central part 20B is rigidly secured to the internal hollow rod 14, the proximal part 20A and the distal part 20C are both rotatable, in opposite directions, around the central part 20B. In rotating the distal and proximal parts 20A and 20C around the central part 20B, in a first direction, it respectively screws/unscrews the distal and proximal parts 21A, 20C around the central part 20B. In rotating the distal and proximal parts 20A and 20C around the central part 20B, in a second direction, it respectively unscrews/screws the distal and proximal parts 21A, 20C around the central part 20B. In order to screw/unscrew both distal and proximal parts 21A, 20C, one has to rotate them in opposite directions. The screwing of the distal part 20A enables the securing of the illuminating device 16. The screwing of the proximal part 20C enables the securing of the external rod 12.

The handle 20 further comprises two openings 28, 30 (see FIGS. 3*b*, 4 and 5), a first opening 28 connected to the inside of the internal hollow rod 14 and a second opening 30 connected to the inside of the external hollow rod 12.

The first opening 28 of the handle 20 is designed to receive, in a sealed way, the illuminating device 16, in order to introduce it at least partially inside the hollow internal rod 14. It might be recovered by a septum. The second opening 30 of the handle 20 is designed to be connected to the pumping device 22 in order to circulate fluid from the fluid reservoir 23 through the external hollow rod 12 in both direction towards and from the inflatable balloon 18.

The second opening 30 comprises a valve 32 (see FIGS. 3*b*, 4 and 5) in order to control, either manually or by means of the control unit 26, the fluid flow in either direction, from the fluid reservoir 23 to the inflatable balloon 28 and from the inflatable balloon 28 to the fluid reservoir 23. In case the valve 32 is to be activated manually, it comprises a wing or handle like element in order to allow the operator to open/close it with a simple movement. In some specific embodiment, the valve 32 is a spontaneous non automatic valve, meaning that it is activated by purely mechanicals means, requiring no intervention neither of the control unit 26 nor of the operator. In one of those embodiments, the valve is a so called comprises a piece of soft deformable material completely inserted inside the second opening 30, forming a tight plug and thus closing the second opening 30. In order to allow the passage of fluid through the second opening 30, said soft deformable plug comprises a central slit which enables an operator to push the needle of a syringe through the plug with no need to manually open or close the valve 32, thus needing less movements to manipulate the system 10. When the syringe is retrieved, the surfaces of the slit merge together and the plug is tight again. A known valve corresponding to this description is the "needle-free swabable valve" by Nordson Medical.

In some embodiments, the system 10 is either partly or entirely discardable.

In order to be handy, quick and easy to use, the handle 20, the external hollow rod 12 and the internal hollow rod 14 are designed to be sealingly secured to each other in one single screwing movement. More precisely, an operator can thus simply place one hand around the handle 20 and one hand around the distal extremity 12D of the external hollow rod 12, and in exerting two opposite rotative movements, they might seal the elements together. The system 10 according to the present invention. enables to implement a method for preparation for treatment by photodynamic therapy, the method comprising performing the steps of:

inserting the internal hollow rod 14 inside the external hollow rod 12, connecting the handle 20 on the external hollow rod 12, inserting at least partially the illuminating device 16 inside the internal hollow rod 14, through the first opening 28 of the handle 20, positioning and/or locking the illuminating device 16 at a predetermined distance from the tip T of the distal extremity 14D of the internal hollow rod 14, sealingly securing the handle 20, the internal hollow rod 14 and the external hollow rod 12, connecting the second opening 30 of the handle 20 to the pumping device 22 and the fluid reservoir 23, preferably a light diffusing solution reservoir, connecting the illuminating device 16 to the laser light source, vacuuming, by means of the pumping device 22, the inflatable balloon 18 in order to completely emptying it and enable a precise determination of the size of the emptied inflatable balloon 18 in order to set a referential, filling, by means of the pumping device 22 and the fluid reservoir 23, the inflatable balloon 18 with a given volume V of fluid, preferably light diffusing solution, until the outer surface of the inflatable balloon 18 reaches the tissues delimiting the patient's body cavity 100 and presses against it, determining the necessary illumination time for providing a determined dose of light energy, said dose ranging from about 1 $J/cm^2$ to about 40 $J/cm^2$, by means of the transfer function (see FIG. 5).

The present invention also relates to a method of treating cancer in a patient in need thereof, by photodynamic therapy, using the system 10 according to the present invention.

In one embodiment, the method comprises the steps of:

administering a photosensitizer compound or a precursor thereof, as defined above, to the patient, thereby having the cells of the tissues delimiting the patient's body cavity 100 absorb said photosensitizer compound or precursor thereof;

providing the system 10 described hereinabove or preparing the system 10 according to the here-above detailed method, positioning the inflatable balloon 18 of the system 10 in a body cavity 100 of the patient activating the illuminating device 16, preferably for a predetermined illumination time for providing a predetermined dose of light energy, disactivating the illuminating device 16, optionally, repeating once or several times the two previous steps for a predetermined amount of time, if needed.

In one embodiment, administration of the photosensitizer compound or precursor thereof may be per os (i.e., by oral route) or parenteral, such as by injection, for example, by intra-arterial, intra-articular, intracardiac, intramuscular, intraperitoneal or intravenous injection.

An example of implementation for both cancer treatment methods might be an "always-on" illumination.

A further example of implementation for both cancer treatment methods might be a succession of on/off illuminations, such as, e.g., 2 minutes of illumination time followed by 2 minutes without illumination, again followed by 2 minutes of illumination time, etc.

In order to release the pressure exerted by the inflatable balloon 18 in its expanded state against the tissues delimiting the patient's body cavity 100, the inflatable balloon 18 may be deflated between two activations of the illuminating device 16. Thus, when the illumination device is not activated, the inflatable balloon 18 is not pushing against the tissues delimiting the patient's body cavity 100. This is enabled by the pumping device 22.

The system 10 according to the present invention enables to deliver the necessary energy dose independently from the volume V of the inflatable balloon 18, meaning independently of the size of the body patient's cavity 100. It is thus possible to treat cavities 100 of all possible sizes. The illumination time can also be adjusted to the power of the laser light source, enabling the system 10 to be used in any kind of conditions. The light source may be controlled by a control unit 26. This control unit 26 may be a computer.

In addition, thanks to a simple and reliable control of the delivered dose of light energy offered by the system 10 according to the present invention, the treatment can be easily reproducible. The efficiency of the treatment by photodynamic therapy is thereby enhanced.

The system according to the is also very easy to assemble, with a minimal number of pieces which are, additionally, easy and convenient to seal together, thus improving the use of the system 10 its efficiency around the operation table and during operation time. The system 10 is entirely to be used manually with no need to any additional system to assemble and use it. Once the light source has been programmed (for example by means of the control unit 26), the system 10 is configured to be operated entirely manually by an operator.

In one embodiment, the method of treating cancer may be performed only once, or may be performed more than once, e.g., with a delay of several weeks, months or years between each photodynamic therapy session.

In one embodiment, the treatment of cancer by photodynamic therapy may further be combined with an immunotherapy treatment. Such combination is known in the art as photoimmunotherapy (PIT).

The present invention also relates to a kit, in particular a kit suitable for performing photodynamic therapy, comprising:

the system 10;

at least one photosensitizer compound; and optionally, instructions for use.

The invention claimed is:

1. A system for a photodynamic therapy treatment of a patient's body cavity configured to provide a predetermined dose of light energy to said cavity, the cavity being delimited by tissues comprising cells having a photosensitizer compound or a precursor thereof absorbed therein, the system comprising:

an external hollow rod extending along a central axis and displaying a distal extremity, an internal hollow rod configured to be inserted inside the external hollow rod, the internal hollow rod extending along the central axis and displaying a distal extremity, the distal extremity being at least partially transparent, an inflatable balloon secured on the distal extremity of the external hollow rod, the inside of the inflatable balloon being in fluidic communication with the inside of the external hollow rod, the inflatable balloon displaying a symmetry of revolution around the central axis, and being designed to either be vacuumized, or be filled, in a controlled way, with a fluid up to a given volume, a handle comprising two openings, a first opening connected to the inside of the internal hollow rod and a second opening connected to the inside of the external hollow rod, wherein the inside of the internal hollow rod is isolated from the inside of the external hollow rod, wherein the first opening of the handle is designed to receive, in a sealed way, an illuminating device intended for illuminating the inflatable balloon, the illuminating device being designed to emit a light adapted to activate the photosensitizer compound, wherein the second opening of the handle is designed to be connected to a pumping device, wherein the handle is made of one single piece comprising a central part, a proximal part and a distal part aligned along the central axis, wherein the central part is rigidly secured to the proximal extremity of the internal hollow rod, wherein the proximal part is rotatable around the central part to sealingly secure the illuminating device, wherein the distal part is rotatable around the central part to sealingly secure the proximal extremity of the external hollow rod, wherein the handle, the external hollow rod and the internal hollow rod are designed to be sealingly secured to each other in one single screwing movement of the distal part and the central part, wherein a given illumination time is determined by means of a transfer function relating each given volume of the inflatable balloon to at least one corresponding distribution of light power at the outer surface of the inflatable balloon and a corresponding illumination time for providing the predetermined dose of light energy.

2. The system according to claim 1, wherein the inflatable balloon is adapted to allow diffusion of the light emitted by the illuminating device.

3. The system according to claim 1, wherein the inflatable balloon has a variable capacity, the balloon being elastic and reversibly extendible, the inflatable balloon presenting a plurality of inflated states depending on the amount of fluid comprised inside the inflatable balloon.

4. The system according to claim 3, wherein the transfer function relates the volume of each inflated state of the inflatable balloon with the corresponding illumination time for providing a determined dose of light energy.

5. The system according to claim 1, wherein the inflatable balloon displays an elongated shape.

6. The system according to claim 1, wherein the distal extremity of the internal hollow rod is designed to be in permanent contact with the inflatable balloon.

7. The system according to claim 6, wherein the internal hollow rod comprises a slidable element, slidable along the central axis, in order to enable a permanent contact between the inflatable balloon and the distal extremity of the internal hollow rod.

8. The system according to claim 1, wherein the internal hollow rod comprises a positioning device adapted to lock a distal extremity of the illuminating device inserted inside the internal hollow rod at a desired distance from the tip of the distal extremity of the internal hollow rod.

9. The system according to claim 1, wherein the internal hollow rod is flexible.

10. The system according to claim 1, wherein the internal hollow rod displays centering means aimed at centering said internal hollow rod with regards to the central axis.

11. The system according to claim 1, wherein the proximal part and the distal part are both rotatable, in opposite directions, around the central part.

12. The system according to claim 11, wherein in order to screw or unscrew the distal part, one has to rotate it in a first direction, and in order to screw or unscrew the proximal part, one has to rotate it in a second direction, opposite to the first direction.

13. A kit for a photodynamic therapy treatment of a patient's body cavity configured to provide a predetermined dose of light energy to said cavity, wherein the kit comprises a system according to claim 1, an illumination device configured to be inserted in said system and a control unit configured to control the illumination device.

14. A method for preparation of a system for photodynamic therapy treatment according to claim 1, the method comprising repeatedly performing steps of:

inserting the internal hollow rod inside the external hollow rod, connecting the handle on the external hollow rod, inserting the illuminating device inside the internal hollow rod, through the first opening of the handle, positioning and/or locking the illuminating device at a predetermined distance from the tip of the distal extremity of the internal hollow rod, sealingly securing the handle, the internal hollow rod and the external hollow rod, connecting the second opening of the handle to the pumping device, vacuuming, by means of the pumping device, the inflatable balloon in order to completely emptying it and enable a precise determination of the size of the emptied balloon in order to set a referential, filling, by means of the pumping device, the inflatable balloon with a given volume fluid, and determining the illumination time by means of the transfer function.

15. A method for treating cancer by photodynamic therapy in a patient in need thereof, the method comprising the steps of:

administering a photosensitizer compound or a precursor thereof to the patient;

providing a system according to claim 1 or preparing said system by a method comprising repeatedly performing steps of:

inserting the internal hollow rod inside the external hollow rod, connecting the handle on the external hollow rod, inserting the illuminating device inside the internal hollow rod, through the first opening of the handle, positioning and/or locking the illuminating device at a predetermined distance from the tip of the distal extremity of the internal hollow rod, sealingly securing the handle, the internal hollow rod and the external hollow rod, connecting the second opening of the handle to the pumping device, vacuuming, by means of the pumping device, the inflatable balloon in emptied balloon in order to set a referential, filling, by means of the pumping device, the inflatable balloon with a given volume fluid, and determining the illumination time by means of the transfer function;

positioning the inflatable balloon of the system in a body cavity of the patient, activating the illuminating device;

disactivating the illuminating device;

optionally, repeating once or several times the two previous steps.

16. The method according to claim 15, wherein the inflatable balloon is deflated between two activations of the illuminating device.

17. The method according to claim 15, wherein the method further comprises treating the patient with an immunotherapy treatment before, concomitantly with and/or after photodynamic therapy.

* * * * *